United States Patent
Estell

(10) Patent No.: US 7,078,216 B2
(45) Date of Patent: Jul. 18, 2006

(54) PROTEASES FROM GRAM POSITIVE ORGANISMS

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 560 days.

(21) Appl. No.: 10/285,074

(22) Filed: Oct. 31, 2002

(65) Prior Publication Data

US 2003/0078177 A1 Apr. 24, 2003

Related U.S. Application Data

(62) Division of application No. 09/555,062, filed as application No. PCT/US98/27018 on Dec. 17, 1998, now Pat. No. 6,528,255.

(30) Foreign Application Priority Data

Dec. 30, 1997 (GB) .................................... 9727466

(51) Int. Cl.
- C12N 9/54 (2006.01)
- C12S 11/00 (2006.01)
- C12S 13/00 (2006.01)
- A23L 1/48 (2006.01)

(52) U.S. Cl. ...................... 435/221; 435/262; 435/263; 426/63

(58) Field of Classification Search ................ 435/221, 435/262, 263; 426/63
See application file for complete search history.

(56) References Cited

U.S. PATENT DOCUMENTS

| | | | |
|---|---|---|---|
| 3,817,837 A | 6/1974 | Rubenstein et al. | 195/103.5 |
| 3,850,752 A | 11/1974 | Schuurs et al. | 195/103.5 |
| 3,939,350 A | 2/1976 | Kronick et al. | 250/365 |
| 3,996,345 A | 12/1976 | Ullman et al. | 424/12 |
| 4,261,868 A | 4/1981 | Hora et al. | 252/529 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,404,128 A | 9/1983 | Anderson | 252/546 |
| 4,533,359 A | 8/1985 | Kondo et al. | 8/128 |
| 4,816,567 A | 3/1989 | Cabilly et al. | 530/387 |
| 5,147,642 A | 9/1992 | Lotz et al. | 424/94.61 |
| 5,204,015 A | 4/1993 | Caldwell et al. | 252/174.12 |
| 5,264,366 A | 11/1993 | Ferrari et al. | 435/252.31 |
| 5,314,692 A | 5/1994 | Haarasilta et al. | 424/94.2 |
| 5,585,253 A | 12/1996 | Doi et al. | 435/172.3 |
| 5,612,055 A | 3/1997 | Bedford et al. | 424/442 |

FOREIGN PATENT DOCUMENTS

| | | |
|---|---|---|
| EP | 0 134 267 B1 | 8/1989 |
| EP | 0 344 250 | 5/1993 |
| EP | 0 369 817 B1 | 4/1996 |
| WO | WO 88/06623 | 9/1988 |
| WO | WO 89/10976 | 11/1989 |
| WO | WO 95/10615 | 4/1995 |
| WO | WO 95/14099 | 5/1995 |

OTHER PUBLICATIONS

Kunst, F., et al. (1997) Accession No. Z99109 and O07598.*
Ausubel et al., Current Protocols in Molecular Biology, John Wiley & Sons, Inc., vol. 1, Ch. and 9, 1987.
Bakhiet et al., "Studies on Transfection and Transformation of Protoplasts of *Bacillus larvae, Bacillus subtilis*, and *Bacillus popilliae*," Applied and Environmental Microbiology, vol. 49, No. 3, pp. 577-581, Mar., 1985.
Benton et al., "Steering λgt Recombinant Clones by Hybridization to Single Plaques in situ," Science, vol. 196, No. 4286, pp. 180-182, Apr. 8, 1977.
Chang et al., "High Frequency Transformation of *Bacillus subtilis* Protoplasts by Plasmid DNA," Molec. Gen. Genet., vol. 168, pp. 111-115, 1979.
Contente et al., "Marker Rescue Transformation by Linear Plasmid DNA in *Bacillus subtilis*," Plasmid, vol. 2, pp. 555-571, 1979.
Fischer et al., "Introduction of plasmid pC194 into *Bacillus thuringiensis* by Protoplast transformation and plasmid transfer," Arch. of Microbiol., vol. 139, pp. 213-217, 1984.
Grunstein et al., "Colony hybridization: A method for the isolation of cloned DNAs that contain a specific gene," Proc. Nat. Acad. Sci. USA, vol. 72, No. 10, pp. 3961-3965, Oct., 1975.
Haima, Peter et al., "Novel plasmid marker rescue transformation system for molecular cloning in *Bacillus subtilis* enabling direct selection of recombinants," Mol. Gen. Genet., vol. 223, pp. 185-191, 1990.
Holubova et al., "Transfer of Liposome-Encapsulated Plasmid DNA to *Bacillus subtilis* Protoplasts and Calcium-Treated *Escherichia coli* Cells," Folia Microbiol., vol. 30, pp. 97-100, 1985.
Kroll et al., "A Multifunctional Prokaryotic Protein Expression System: Overproduction, Affinity Purification, and Selective Detection," DNA and Cell Biology, vol. 12, No. 5, pp. 441-453, 1993.

(Continued)

*Primary Examiner*—Charles L. Patterson, Jr.
(74) *Attorney, Agent, or Firm*—Genencor International, Inc.

(57) ABSTRACT

The present invention relates to the identification of a novel metalloproteases in gram positive microorganisms. The present invention provides the nucleic acid and amino acid sequences for the metalloprotease. The present invention also provides host cells having a mutation or deletion of part or all of the gene encoding the metalloprotease. The present invention provides host cells which further comprises a nucleic acid encoding desired heterologous proteins such as enzymes. The present invention also provides cleaning compositions, animal feeds and compositions used to treat a textile that include the metalloprotease of the present invention.

8 Claims, 8 Drawing Sheets

OTHER PUBLICATIONS

Kunst, F. et al., "The complete genome sequence of the Gram-positive bacterium *Bacillus subtilis*," Nature, vol. 390, pp. 249-264, Nov. 20, 1997.

Maddox et al., "Elevated Serum Levels in Human Pregnancy of a Molecule Immunochemically Similar to Eosinophil Granule Major Basic Protein," J. Exp. Med., vol. 158, pp. 1211-1226, Oct., 1983.

Mann et al., "Transformation of *Bacillus spp.*: an Examination of the Transformation of *Bacillus* Protoplasts by Plasmids pUB110 and pHV33." Current Microbiology, vol. 13, pp. 191-195, 1986.

Margot, Philippe et al., "The *wprA* gene of *Bacillus subtilis* 168, expressed during exponential growth, encodes a cell-wall-associated protease," Microbiology, vol. 142, pp. 3437-3444, 1996.

Margot, Philippe et al., "The gene of the N-acetylglucominidase, a *Bacillus subtilis* 168 cell wall hydrolase not involved in vegetative cell autolysis," Mol. Microbiology, vol. 12, pp. 535-545, 1994.

McDonald et al., "Plasmid Transformation of *Bacillus sphaericus* 1593," Journal of General Microbiology, vol. 130, pp. 203-208, 1984.

Murray et al., "Codon usage in plant genes," Nucleic Acids Research, vol. 17, No. 2, pp. 477-498, 1989.

Porath, Jerker "Immobilized Metal Ion Affinity Chromatography," Protein Expression and Purification, vol. 3, pp. 263-281, 1992.

Sadaie et al., "Nucleotide sequence and analysis of the phoB-rrnE-groESL region of the *Bacillus subtilis* chromosome," Microbiology, vol. 143, pp. 1861-1866, 1997.

Smith, Michael et al., "Protoplast Transformation in Coryneform Bacteria and Introduction of an α-Amylase Gene from *Bacillus amyloliquefaciens* into *Brevibacterium lactofermentum*," Applied and Environmental Microbiology, vol. 51, No. 3, pp. 634-639, Mar., 1986.

Vorobjeva, I.P. et al., "Transformation of *Bacillus megaterium* Protoplasts by Plasmid DNA," FEMS Microbiology Letters 7, pp. 261-263, 1980.

Ward, Owen, P. et al., "Proteinases, In Microbiol Enzymes and Biotechnology," (W. M. Fogerty, ed), Applied Science, London, pp. 251-317, 1983.

Weinrauch et al., "Plasmid Marker Rescue Transformation Proceeds by Breakage-Reunion in *Bacillus subtilis*," Journal of Bacteriology, vol. 169, No. 3, pp. 1205-1211, Mar., 1987.

\* cited by examiner

```
TCCGTCGCGATTGGCCTTTTGGTGACAACCCTCGCAGCTGTGATGATGCTTTAAAACAG
    |         |         |         |         |         |       60
AGGGCAGCCGCTAACCGGAAAACCACTGTTGGGAGCGTCGACACTACGAAATTTGTC

CATGAGTTGAAATATTCAGACTTTTTCTATACAATCATGGAAAAGCATAGAAAAGGGGGA
    |         |         |         |         |         |      120
GTACTCAACTTTATAAGTCTGAAAAAGATATGTTAGTACCTTTTCGTATCTTTTCCCCT

AGCGGGCTTTGTCCATATCCCACACTGCAGAAAGAGATAAACAAACAGCTCGACGGCTGTTT
    |         |         |         |         |         |      180
TCGCCCGAAACAGGTATAGGGTGTGACGTCTTTCTCTATTTGTTTGTCGAGCTGCCGACAAA
                                      L  S  I  S  T  L  Q  K  E  I  N  K  Q  L  D  G  C  F
                                                                                    yhaA TGAAGAAATGGTTGAGATCAGGCGCCATTTTCATATGTATCCTGAGCTCTCATTTCAAGA
    |         |         |         |         |         |      240
ACTTCTTTACCAACTCTAGTCCGCGGTAAAAGTATACATAGGACTCGAGAGTAAAGTTCT
 E  E  M  V  E  I  R  R  H  F  H  M  Y  P  E  L  S  F  Q  E
                                      yhaA
```

FIG._1A

```
AGAAAAAACCGCGCATTTATTGCTTCCTATTATGAATCGTTAGGAGTCCCAATCCGCAC
     ----+----+----+----+----+----+----+----+----+----+----+----+  300
TCTTTTTTGGCGCGTAAATAACGAAGGATAATACTTAGCAATCCTCAGGGTTAGGCGTG
  E  K  T  A  A  F  I  A  S  Y  Y  E  S  L  G  V  P  I  R  T
                              ───────────────yhaA───────────────

AAACGTTGGGCGGTAGAGGGGTTTTAGCAAATATAGAAGGAAGCGAACCCGGCCCTACAGT
     ----+----+----+----+----+----+----+----+----+----+----+----+  360
TTTGCAACCCGCCATCTCCCCAAAATCGTTTATATCTTCCTTCGCTTGGGCCGGGATGTCA
  N  V  G  G  R  G  V  L  A  N  I  E  G  S  E  P  G  P  T  V
                              ───────────────yhaA───────────────

CGCTTTGAGGGCCGACTTTGACGCTCTCTCCCATTCAAGATGAAAAAGATGTCCCTTACGC
     ----+----+----+----+----+----+----+----+----+----+----+----+  420
GCGAAACTCCCGGCTGAAACTGCGAGAGGGTAAGTTCTACTTTTTCTACAGGGAATGCG
  A  L  R  A  D  F  D  A  L  P  F  K  M  K  K  D  V  P  Y  A
                              ───────────────yhaA───────────────

CTCCAAAAGTGCCTGGTCGTCATGCATGGGCCACGACGGCCACACCGCAGCTCTTCT
     ----+----+----+----+----+----+----+----+----+----+----+----+  480
GAGGTTTCACGGACCAGCAGTACGTACGCCGGTGCTGCCGGTGTGGGCGTGAGAAGA
  S  K  V  P  G  V  M  H  A  C  G  H  D  G  H  T  A  A  L  L
                              ───────────────yhaA───────────────
```

FIG._1B

```
CGCAGTGGCCAAGGTCCTTCACCAAAAACAGAGACATGAACTGAAGGGAACATTTGTGATGAT
       +         +         +         +         +         +        540
GCGTCACCGGTTCCAGGAAGTGGTTTTGTCTCTGTACTTGACTTCCCTTGTAAACACTACTA

A   V   A   K   V   L   H   Q   N   R   H   E   L   K   G   T   F   V   M   I
                                           ─────────────────────────────────────
                                                        yhaA CCACCAGCATGCAGAAGAATATTATCCTGGAGGCGCAAAGCCAATGATTGATGACGGATG
       +         +         +         +         +         +        600
GGTGGTCGTACGTCTTCTTATAATAGGACCTCCGCGTTTCGGTTACTAACTACTGCCTAC H   Q   H   A   E   E   Y   Y   P   G   G   A   K   P   M   I   D   D   G   C
─────────────────────────────────────────────────────────────────────────────────
                                    yhaA TCTCGAAAACACGGATGTGATATTCGGCACTCATCTTTGGGCAACTGAGCCGCTCGGAAC
       +         +         +         +         +         +        660
AGAGCTTTTGTGCCTACACTATAAGCCGTGAGTAGAAACCCGTTGACTCGGCGAGCCTTG L   E   N   T   D   V   I   F   G   T   H   L   W   A   T   E   P   L   G   T
─────────────────────────────────────────────────────────────────────────────────
                                    yhaA TATTCTCTGCCGCCCCGGCGCCGTAATGGCGGCCAGACCGATTTACGATTAAAGTCTT
       +         +         +         +         +         +        720
ATAAGAGACGGCGGGGCCGCGGCATTACCGCCGGTCTGGCTAAATGCTAATTTCAGAA I   L   C   R   P   G   A   V   M   A   A   A   D   R   F   T   I   K   V   F
─────────────────────────────────────────────────────────────────────────────────
                                    yhaA
```

*FIG._1C*

```
CGGAAAGGGCGGCCACGGGCGCTCATCCGCATGATACTAAAGACGCCGTCCTAATCGGTTC
         +         +         +         +         +         +    780
GCCTTTCCCGCCGGTGCCCGCGAGTAGGCGTACTATGATTTCTGCGGCAGGATTAGCCAAG
   G  K  G  G  H  G  A  H  P  H  D  T  K  D  A  V  L  I  G  S
                                     ────────────────────────
                                                   yhaA GCAAATCGTTTCCTCTCTTTTGCAGCACATTGTCAGCCGCAAAGTCAATCCGATTCAATCCGC
         +         +         +         +         +         +    840
CGTTTAGCAAAGGAGAGAAAACGTCGTGTAACAGTCGGCGTTTCAGTTAGGCTAAGTTAGGCG
   Q  I  V  S  S  L  Q  H  I  V  S  R  K  V  N  P  I  Q  S  A
  ───────────────────────────────────────────────────────────
                        yhaA CGTCATTTCGACAGGCTCCTTCATCGCCGACAATCCGTTTAATGTCATCGCAGACCAAGC
         +         +         +         +         +         +    900
GCAGTAAAGCTGTCCGAGGAAGTAGCGGCTGTTAGGCAAATTACAGTAGCGTCTGGTTCG
   V  I  S  T  G  S  F  I  A  D  N  P  F  N  V  I  A  D  Q  A
  ───────────────────────────────────────────────────────────
                        yhaA AGTACTCATCGGCACAGCCGTTCTTTTGATGAAAATGTCCGGACATTCTGGAGAAAGA
         +         +         +         +         +         +    960
TCATGAGTAGCCGTGTCGGCAAGAAAACTACTTTTACAGGCCCTGTAAGACCTCTTTCT
   V  L  I  G  T  A  R  S  F  D  E  N  V  R  D  I  L  E  K  E
  ───────────────────────────────────────────────────────────
                        yhaA
```

*FIG._1D*

```
AATTGAAGCCGGTTGTAAAGGAATATGCAGCATGCACGGCCGTCCTATGAGTACACCTA
        +         +         +         +         +         +      1020
TTAACTTCGCCAACATTTCCTTATACGTCGTACGTGCCGGCAGGATACTCATGTGGAT

I  E  A  V  V  K  G  I  C  S  M  H  G  A  S  Y  E  Y  T  Y
                                    ─────────────yhaA─────────────

TGAACAGGGTTATCCAGCGGTTGTGAACCATCCTGCAGAAACGAACCACTTGGTGAGCAC
        +         +         +         +         +         +      1080
ACTTGTCCCAATAGGTCGCCAACACTTGGTAGGACGTCTTTGCTTGGTGAACCACTCGTG

E  Q  G  Y  P  A  V  V  N  H  P  A  E  T  N  H  L  V  S  T
                            ─────────────yhaA─────────────

CGCAAAGAATACCGAGGGCGTTCAGCAGGTCATTGACGGTGAACCACAAATGGGCGGCGA
        +         +         +         +         +         +      1140
GCGTTTCTTATGGCTCCCGCAAGTCGTCCAGTAACTGCCACTTGGTGTTTACCCGCCGCT

A  K  N  T  E  G  V  Q  Q  V  I  D  G  E  P  Q  M  G  G  E
                                    ─────────────yhaA─────────────

GGATTTTGCTTATTACTTACAAAACGTGAAGGGCACTTTTTTCTTTACAGGCGCCGCTCC
        +         +         +         +         +         +      1200
CCTAAAACGAATAATGAATGTTTTGCACTTCCCGTGAAAAAGAAATGTCCGCGGCGAGG

D  F  A  Y  Y  L  Q  N  V  K  G  T  F  F  F  T  G  A  A  P
                                    ─────────────yhaA─────────────
```

*FIG._1E*

```
CGAACAGCCAGAGCGAGTCTATTCCCACCATCCGAAATTTGATATCAACGAAAAAGC
----+----+----+----+----+----+----+----+----+----+----+----  1260
GCTTGTCGGTCTCGCTCAGATAAGGGTGGTAGGCTTTAAACTATAGTTGCTTTTCG

E  Q  P  E  R  V  Y  S  H  H  P  K  F  D  I  N  E  K  A
                              |————— yhaA —————————————————

CATGCTGACAGCGGCCAAGGTCCTTGCCGGCTGCCGATCACCTATCATCAGCTATAAAA
----+----+----+----+----+----+----+----+----+----+----+----  1320
GTACGACTGTCGCCGGTTCCAGGAACGGCCGCGACGCTAGTGGATAGTAGTCGATATTT

M  L  T  A  A  K  V  L  A  G  A  A  I  T  Y  H  Q  L
——————————————————————————————————————————————————— |
                              yhaA AAACAGCCGGAGTGTTTATTCTCCGGCTGTTCCTTTAATATCCTCAGATGAAAAACATG
----+----+----+----+----+----+----+----+----+----+----+----  1380
TTTGTCGGCCTCACAAATAAGAGGCCGACAAGGAAATTATAGGAGTCTACTTTTTGTAC TCTTGCCGTTTCTCCAAGCTGAGCAAGCAGCTTATAATTGGCAATTCCGCCGACTGCCGC
----+----+----+----+----+----+----+----+----+----+----+----  1440
AGAACGGCAAAGAGGTTCGACTCGTTCGTCGAATATTAACCGTTAAGGCGGCTGACGGCG

TCCTACGCCC
————————→  1450
AGGATGCGGG
```

*FIG._1F*

```
ID    HIPO_CAMJE    STANDARD;    PRT;    383 AA.
DE    HIPPURATE HYDROLASE (EC 3.5.1.32) (BENZOYLGLYCINE AMIDOHYDROLASE)
DE    (HIPPURICASE).
GN    HIPO.
OS    CAMPYLOBACTER JEJUNI.
CC    -!- CATALYTIC ACTIVITY: HIPPURATE + H(2)O = BENZOATE + GLYCINE.
CC    -!- SIMILARITY: BELONGS TO PEPTIDASE FAMILY M40, ALSO KNOWN AS THE
CC        AMA/HIPO/HYUC FAMILY OF HYDROLASES.
DR    EMBL; Z36940; G535810; -.
KW    HYDROLASE.
SQ    SEQUENCE    383 AA;    42590 MW;    A123937C CRC32;

[NOTE: generally conserved residues are D104, E134, E135, H195,
and E331 using hipo_camje numbering. - DAE]

YhaA: 396 AA - 1080 kb - Function unknown; similar to aminoacylase from
B. stearothermophilus hipo_camje.pep
BSUPEP:YHAA YhaA 396 AA - 1080 kb SCORES    Init1: 310    Initn: 622    Opt: 746    z-score: 848.5    E(): 5.6e-42
Smith-Waterman score: 746;    34.9% identity in 387 aa overlap 10         20           30         40         50         60
hipo_camje.p    MNLIPEILDLQGEFEK---IRHQIHENPELGFDELCTAKLVAQKLKEFGYEVYEEI
                |  ||: ||:  |:|    |: | :|:|| |  | ::|: :|: ::|:  |: :::
YhaA    MSISTLQKEINKQLDGCFEEMVEIRRHFHMYPELSFQEEKTAAFIASYYESLGVPIRTNV
                       10         20           30         40         50         60
```

FIG._2A

```
                          60            70           80            90          100           110
hipo_camje.p  GKTGVVGVLKKGNSDKKIGLRADMDALPLQECTNLPYKSKKENVMHACGHDGHTTSLLLA
              :::: ::      ::|||||     :: ::::         :|||||||||||||||| ::
YHAA          GGRGVLANIEGSEPGPTVALRADFDALPFKMKKDVPYASKVPGVMHACGHDGHTAALLAV
                  70            80           90           100          110         120

120           130          140           150          160
hipo_camje.p  AKYLASQN---FNGTLNLYFQPAEEGL-GGAKAMIEDGLFEKFDSDYVFG---WHNMPFG
              ::: :      ::|:: :       :|  ||| |  :       ::: ||     :  ||
YHAA          AKVL-HQNRHELKGTFVMIHQHAEEYYPGGAKPMIDDGCLE--NTDVIFGTHLWATEPLG
                  130          140           150          160          170

170           180          190           200          210          220
hipo_camje.p  SDKKFYLKKGAMMASSDSYSIEVIGRGGHGSAPEKAKDPIYAASLLVVALQSIVSRNVDP
              :  :    ||  ::   :|:|:     : :||||| ::| :|:|:  :|||:::
YHAA          T---ILCRPGAVMAAADRFTIKVFGKGGHGAHPHDTKDAVLIGSQIVSSLQHIVSRKVNP
                  180          190           200          210          220         230

230           240          250           260          270          280
hipo_camje.p  QNSAVVSIGAFNAGHAFNIIPDIVTIKMSVRALDNETRKLTEEKIYKICKGLAQANDIEI
              :::|:|:||  |   |::|: ||::|     |||   :|::| :||:||   ::
YHAA          IQSAVISTGSFIADNPFNVIADQAVLIGTARSFDENVRDILEKEIEAVVKGICSMHGASY
                  240          250           260          270          280         290

290           300          310           320          330          340
hipo_camje.p  KINKNVVAPVTMNNDEAVDFASEVAKELFGEKNCEFNHRPLMASEDFGFFCEMKKCAYAF
              :  ::|    :: :::||: :|   ::::| :     :  ::|| ||:  ||::    |
YHAA          EYTYEQGYPAVVNHPAETNHLVSTAKNTEGVQQV-IDGEPQMGGEDFAYYLQNVKGTFFF
                  300          310           320          330         340          350

350           360          370           380
hipo_camje.p  L----ENENDIYLHNS-SYVFNDKLLARAASYYAKLALKYLK
                   ::: :  |::|  :: |:::       :|: |::|
YHAA          TGAAPEQPERVYSHHHPKFDINEKAMLTAAKVLAGAAITYHQL
                  360          370           380         390
```

PROTEASES FROM GRAM POSITIVE ORGANISMS

The present application is a Divisional of U.S. patent appln. Ser. No. 09/555,062, filed May 23, 2000, now U.S. Pat. No. 6,528,255, issued Mar. 4, 2003, which is a 371 of PCT/US98/27018, filed Dec. 17, 1998. The present application also claims priority to PCT/US98/27018, filed Dec. 17, 1998, and GB Appln. No. 9727466, filed Dec. 30, 1997, now abandoned.

FIELD OF THE INVENTION

The present invention relates to metalloproteases derived from gram positive microorganisms. The present invention provides nucleic acid and amino acid sequences of a metalloproteases identified in *Bacillus*. The present invention also provides methods for the production of the metalloprotease in host cells as well as the production of heterologous proteins in a host cell having a mutation or deletion of part or all of the metalloprotease of the present invention.

BACKGROUND OF THE INVENTION

Gram positive microorganisms, such as members of the group *Bacillus,* have been used for large-scale industrial fermentation due, in part, to their ability to secrete their fermentation products into the culture media. In gram positive bacteria, secreted proteins are exported across a cell membrane and a cell wall, and then are subsequently released into the external media usually maintaining their native conformation.

Various gram positive microorganisms are known to secrete extracellular and/or intracellular proteases at some stage in their life cycles. Some of these proteases are produced in large quantities for industrial purposes. However, a negative aspect of the presence of proteases in gram positive organisms is their contribution to the overall degradation of secreted heterologous or foreign proteins.

The classification of proteases found in microorganisms is based on their catalytic mechanism which results in four groups: serine proteases, metalloproteases, cysteine proteases, and aspartic proteases. These categories can be distinguished by their sensitivity to various inhibitors. For example, serine proteases are inhibited by phenylmethylsulfonylfluoride (PMSF) and diisopropylfluorophosphate (DIFP); metalloproteases by chelating agents; cysteine proteases by iodoacetamide and heavy metals and aspartic proteases by pepstatin. Further, in general, serine proteases have alkaline pH optima, metalloproteases are optimally active around neutrality, and cysteine and aspartic proteases have acidic pH optima (*Biotechnology Handbooks, Bacillus.* Vol. 2, edited by Harwood, 1989, Plenum Press, New York).

Metalloproteases form the most diverse of the catalytic types of proteases. Family m40 includes bacterial enzymes such as the hippurate hydrolase from *Campylobacter jejuni* (HipO) and the hydantoin utilization protein C (HyuC) from *Pseudomonas sp.*

SUMMARY OF THE INVENTION

The present invention relates to the discovery of a heretofore unknown metalloprotease (MP) found in gram positive microorganisms, uses of the MP in industrial applications, and advantageous strain improvements based on genetically engineering such microorganisms to delete, underexpress or overexpress that MP. The present invention is based upon the discovery that MP has overall amino acid relatedness to *Escherichia coli* pitrilysin.

The present invention is based upon Applicant's discovery of this new metalloprotease, MP (YhaA), which in addition to providing a new and useful protease and methods of detecting DNA encoding other such proteases in a gram positive microorganism, provides several advantages which may facilitate optimization and/or modification of strains of gram positive microorganisms, such as *Bacillus,* for expression of desired, e.g. heterologous, proteins. Such optimizations, as described below in detail, allow the construction of strains that can have decreased proteolytic degradation of desired expression products.

Due to the relatedness of MP to hippurate hydrolase and hydantoin utilization protein C, it can be concluded that MP is also an endopeptidase and would be expected to behave similarly to hippurate hydrolase and hydantoin utilization protein C.

The present invention encompasses the naturally occurring MP encoded by nucleic acid found in a *Bacillus* species as well as the nucleic acid and amino acid molecules having the sequences disclosed in SEQ ID NOS: 1 and 2. In one embodiment, the gram positive microorganism is a *Bacillus*. In a further embodiment, the *Bacillus* is preferably selected from the group consisting of *Bacillus subtilis, Bacillus stearothermophilus, Bacillus licheniformis* and *Bacillus amyloliquefaciens.* The invention further provides for a metalloprotease that has at least 80%, preferably at least 90%, most preferably 95% homology with the amino acid sequence of SEQ ID NO: 2. The invention also provides for a nucleic acid which encodes a metalloprotease that has at least 80%, preferably at least 90%, most preferably 95% homology with the nucleotide sequence shown in SEQ ID NO: 1.

In a preferred embodiment, the present invention encompasses the naturally occurring MP nucleic acid molecule having the sequence found in *Bacillus subtilis* I-168 strain (*Bacillus Genetic Stock Center,* accession number 1A1, Columbus, Ohio) in the region of about 1080 kb from the point of origin. In another preferred embodiment, the *Bacillus subtilis* MP nucleic acid and amino acid molecules have the sequences as shown in FIGS. 1A–1D (SEQ ID NOS: 1 and 2).

The present invention provides isolated polynucleotide and amino acid sequences for *Bacillus subtilis* MP in FIGS. 1A–1D (SEQ ID NOS: 1 and 2). Due to the degeneracy of the genetic code, the present invention encompasses any nucleic acid sequence that encodes the *Bacillus subtilis* MP amino acid sequence. The present invention provides expression vectors and host cells comprising a nucleic acid encoding a gram positive MP. The present invention also provides methods of making the gram positive MP.

The present invention encompasses novel amino acid variations of gram positive MP amino acid sequences disclosed herein that have proteolytic activity. Naturally occurring gram positive MP as well as proteolytically active amino acid variations or derivatives thereof, have application in the textile industry, in cleaning compositions and in animal feed.

The present invention also encompasses amino acid variations or derivatives of gram positive MP that do not have the characteristic proteolytic activity as long as the nucleic acid sequences encoding such variations or derivatives would have sufficient 5' and 3' coding regions to be capable of being integrated into a gram positive organism genome. Such variants would have applications in gram positive expression systems where it is desirable to delete, mutate, alter or otherwise incapacitate the naturally occurring metalloprotease in order to diminish or delete its proteolytic activity. Such an expression system would have the advantage of allowing for greater yields of recombinant heterologous proteins or polypeptides.

The present invention provides methods for detecting gram positive microorganism homologues of *B. subtilis* MP that comprises hybridizing part or all of the nucleic acid encoding *B. subtilis* MP with nucleic acid derived from gram positive organisms, either of genomic or cDNA origin. Accordingly, the present invention provides a method for detecting a gram positive microorganism MP, comprising the steps of hybridizing gram positive microorganism nucleic acid under low stringency conditions to a probe, wherein the probe comprises part or all of the nucleic acid sequence shown in FIGS. 1A–1D (SEQ ID NO:1); and isolating the gram positive nucleic acid which hybridizes to said probe.

The production of desired heterologous proteins or polypeptides in gram positive microorganisms may be hindered by the presence of one or more proteases which degrade the produced heterologous protein or polypeptide. One advantage of the present invention is that it provides methods and expression systems which can be used to prevent that degradation, thereby enhancing yields of the desired heterologous protein or polypeptide.

Accordingly, the present invention provides a gram positive microorganism that can be used as a host cell having a mutation or deletion of part or all of the gene encoding MP, which results in the inactivation of the MP proteolytic activity, either alone or in combination with mutations in other proteases, such as apr, npr, epr, mpr, bpf or isp, or other proteases known to those of skill in the art. In one embodiment of the present invention, the gram positive microorganism is a member of the genus *Bacillus*. In a preferred embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*. In a further preferred embodiment, the *Bacillus* is *Bacillus subtilis*.

In another aspect, the gram positive host cell having one or more metalloprotease deletions or mutations is further genetically engineered to produce a desired protein. In one embodiment of the present invention, the desired protein is heterologous to the gram positive host cell. In another embodiment, the desired protein is homologous to the host cell.

In another embodiment, a host cell is engineered to produce MP. The gram positive microorganism may be normally sporulating or non-sporulating. In a preferred embodiment, the gram positive host cell is a *Bacillus*. In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*. In a further preferred embodiment, the *Bacillus* host cell is *Bacillus subtilis*.

In a further aspect of the present invention, gram positive MP is produced on an industrial fermentation scale in a microbial host expression system. In another aspect, isolated and purified recombinant MP is used in compositions intended for use in the textile industry, in cleaning compositions, such as detergents, and in animal feeds. Accordingly, the present invention provides a cleaning composition, animal feed and a composition for the treatment of a textile comprising MP. The metalloprotease, MP, may be used alone or in combination with other enzymes and/or mediators or enhancers.

As noted, the present invention provides a cleaning composition comprising a metalloprotease, MP, comprising the amino acid sequence shown in SEQ ID NO:2. Also provided are cleaning compositions comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

Further there is provided an animal feed comprising a metalloprotease, MP, comprising the amino acid sequence shown in SEQ ID NO:2. Also provided are animal feeds comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

Also provided is a composition for the treatment of a textile comprising a metalloprotease, MP, comprising the amino acid sequence shown in SEQ ID NO:2. Also provided are compositions for the treatment of a textile comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

BRIEF DESCRIPTION OF THE DRAWINGS

FIGS. 1A–1F show the DNA and amino acid sequence for *Bacillus subtilis* MP (YhaA) (SEQ ID NOS: 1 and 2).

FIGS. 2A–2B show an amino acid alignment of Campylobacter jejuni benzoylglycine amidohydrolase and *Bacillus subtilis* MP (YhaA).

DETAILED DESCRIPTION OF THE PREFERRED EMBODIMENTS

Definitions

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

The present invention relates to a newly characterized metalloprotease (MP) from gram positive organisms. In a preferred embodiment, the gram positive organisms is a *Bacillus*. In another preferred embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

In another preferred embodiment, the gram positive organism is *Bacillus subtilis* and MP has the amino acid sequence encoded by the nucleic acid molecule having the sequence that occurs around 1080 kilobases from the point of origin of *Bacillus subtilis* I-168.

In another preferred embodiment, MP has the nucleic acid and amino acid sequence as shown in FIGS. 1A–1D (SEQ ID NOS: 1 and 2). The present invention encompasses the use of amino acid variations of the amino acid sequences disclosed in FIGS. 1A–1D (SEQ ID NO: 2) that have proteolytic activity. Such proteolytic amino acid variants can be used in the textile industry, animal feed and cleaning compositions. The present invention also encompasses the use of *B. subtilis* amino acid variations or derivatives that are not proteolytically active. DNA encoding such variants can be used in methods designed to delete or mutate the naturally occurring host cell MP.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homologue" as used herein refers to a gram positive microorganism polynucleotide that has at least 80%, preferably at least 90% and more preferably at least 95% identity to *B.subtilis* MP, or which is capable of hybridizing to *B.subtilis* MP under conditions of high stringency and which encodes an amino acid sequence having metalloprotease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in the chosen gram positive host cell. Examples of heterologous proteins include enzymes such as hydrolases including proteases, cellulases, carbohydrases such as amylases, and lipases; isomerases such as racemases, epimerases, tautomerases, or mutases; oxidases, reductases, transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in the chosengram positive host cell. The invention includes host cells producing the homologous protein via recombinant DNA technology. The present invention encompasses a gram positive host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

As used herein, the term "overexpressing" when referring to the production of a protein in a host cell means that the protein is produced in greater amounts than in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

The unexpected discovery of the metalloprotease MP found in translated uncharacterised *B.subtilis* genomic sequences provides a basis for producing host cells, expression methods and systems which can be used to prevent the degradation of recombinantly produced heterologous proteins.

Accordingly, in a preferred embodiment, the host cell is a gram positive host cell that has a deletion or mutation in the naturally occurring nucleic acid encoding MP said mutation resulting in deletion or inactivation of the production by the host cell of the MP proteolytic gene product. The host cell may additionally be genetically engineered to produced a desired protein or polypeptide.

It may also be desired to genetically engineer host cells of any type to produce a gram positive metalloprotease. Such host cells are used in large scale fermentation to produce large quantities of the metalloprotease which may be isolated or purified and used in cleaning products, such as detergents.

I. Metalloprotease Sequences

The present invention encompasses the use of MP polynucleotide homologues encoding gram positive microorganism metalloproteases MP which have at least 80%, preferably at least 90%, more preferably at least 95% identity to *B. subtilis* MP as long as the homologue encodes a protein that has proteolytic activity. A preferred MP polynucleotide homologue has 96% homology to *B. subtilis* MP.

Gram positive polynucleotide homologues of *B. subtilis* MP may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA.

As will be understood by those of skill in the art, the polynucleotide sequence and amino acid sequence disclosed in FIGS. 1A–1D may reflect inadvertent errors inherent to nucleic acid sequencing technology. The present invention encompasses the naturally occurring nucleic acid molecule having the nucleic acid sequence obtained from the genomic sequence of *Bacillus* species.

Nucleic acid encoding *Bacillus subtilis* MP starts around 1080 kilobases counting from the point of origin in the *Bacillus subtilis* strain I-168 (Anagnostopala, 1961, *J. Bacteriol.*, 81:741–746 or *Bacillus Genomic Stock Center*, accession 1A1, Columbus, Ohio). The *Bacillus subtilis* point of origin has been described in Ogasawara, N. (1995, Microbiology 141:Pt.2 257–59). *Bacillus subtilis* MP has a length of 396 amino acids. Based upon the location of the DNA encoding *Bacillus subtilis* MP, naturally occurring *B. subtilis* MP can be obtained by methods known to those of skill in the art including PCR technology.

Oligonucleotide sequences or primers of about 10–30 nucleotides in length can be designed from the polynucleotide sequence disclosed in FIGS. 1A–1D and used in PCR technology to isolate the naturally occurring sequence from *B. subtilis* genomic sequences.

Another general strategy for the "cloning" of *B. subtilis* genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned"

DNA pieces. From the most external DNA sequence, a new round of inverse PCR is started. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.) according to manufacturer's instructions.

Nucleic acid sequences derived from genomic DNA may contain regulatory regions in addition to coding regions. Whatever the source, the isolated MP gene should be molecularly cloned into a suitable vector for propagation of the gene.

In molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the MP may be accomplished in a number of ways. For example, a *B. subtilis* MP gene of the present invention or its specific RNA, or a fragment thereof, such as a probe or primer, may be isolated and labeled and then used in hybridization assays to detect a gram positive MP gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram positive MP polynucleotide homologues which comprises hybridizing part or all of a nucleic acid sequence of *B. subtilis* MP with gram positive microorganism nucleic acid of either genomic or cDNA origin.

Also included within the scope of the present invention is the use of gram positive microorganism polynucleotide sequences that are capable of hybridizing to the nucleotide sequence of *B. subtilis* MP under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*, Vol. 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologues.

The term "hybridization" as used herein shall include "the process by which a strand of nucleic acid joins with a complementary strand through base pairing" (Coombs, J., (1994), *Dictionary of Biotechnology*, Stockton Press, New York, N.Y.).

The process of amplification as carried out in polymerase chain reaction (PCR) technologies is described in Dieffenbach, CW and GS Dveksler, (*PCR Primer, a Laboratory Manual*, Cold Spring Harbor Press, Plainview, N.Y., 1995). A nucleic acid sequence of at least about 10 nucleotides and as many as about 60 nucleotides from *B. subtilis* MP, preferably about 12 to 30 nucleotides, and more preferably about 20–25 nucleotides can be used as a probe or PCR primer.

The *B. subtilis* MP amino acid sequences (shown in FIGS. 1A–1D) were identified via a BLAST search (Altschul, Stephen, Basic local alignment search tool, *J. Mol. Biol.*, 215:403–410) of *Bacillus subtilis* genomic nucleic acid sequences. *B. subtilis* MP (YhaA) was identified by its overall nucleic acid identity to the metalloprotease, succinyl-diaminopimelate desuccinylase from *Escherichia coli*.

II. Expression Systems

The present invention provides host cells, expression methods and systems for the enhanced production and secretion of desired heterologous or homologous proteins in gram positive microorganisms. In one embodiment, a host cell is genetically engineered to have a deletion or mutation in the gene encoding a gram positive MP such that the respective activity is deleted. In another embodiment of the present invention, a gram positive microorganism is genetically engineered to produce and/or overproduce a metalloprotease of the present invention.

Inactivation of a Gram Positive Metalloprotease in a Host Cell

Producing an expression host cell incapable of producing the naturally occurring metalloprotease necessitates the replacement and/or inactivation of the naturally occurring gene in the genome of the host cell. In a preferred embodiment, the mutation is a non-reverting mutation.

One method for mutating a nucleic acid encoding a gram positive metalloprotease is to clone the nucleic acid or part thereof, modify the nucleic acid by site directed mutagenesis and reintroduce the mutated nucleic acid into the cell on a plasmid. By homologous recombination, the mutated gene can be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the metalloprotease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoding the metalloprotease gene. In another preferred embodiment, nucleic acid encoding the catalytic amino acid residues are deleted.

Deletion of the naturally occurring gram positive microorganism metalloprotease can be carried out as follows. A metalloprotease gene including its 5' and 3' regions is isolated and inserted into a cloning vector. The coding region of the metalloprotease gene is deleted from the vector in vitro, leaving behind a sufficient amount of the 5' and 3' flanking sequences to provide for homologous recombination with the naturally occurring gene in the parent host cell.

The vector is then transformed into the gram positive host cell. The vector integrates into the chromosome via homologous recombination in the flanking regions. This method leads to a gram positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the metalloprotease locus. Since illegitimate recombination will give different results, it will be necessary to determine whether the complete gene has been deleted, such as through nucleic acid sequencing or restriction maps.

Another method of inactivating the naturally occurring metalloprotease gene is to mutagenize the chromosomal gene copy by transforming a gram positive microorganism with oligonucleotides which are mutagenic. Alternatively, the chromosomal metalloprotease gene can be replaced with a mutant gene by homologous recombination.

The present invention encompasses host cells having additional protease deletions or mutations, such as deletion of or mutation(s) in the genes encoding apr, npr, epr, mpr and others known to those of skill in the art.

One assay for the detection of mutants involves growing the *Bacillus* host cell on medium containing a protease substrate and measuring the appearance or lack thereof, of a zone of clearing or halo around the colonies. Host cells which have an inactive protease will exhibit little or no halo around the colonies.

III. Production of Metalloprotease

For production of metalloprotease in a host cell, an expression vector comprising at least one copy of nucleic acid encoding a gram positive microorganism MP, and preferably comprising multiple copies, is transformed into the host cell under conditions suitable for expression of the metalloprotease. In accordance with the present invention, polynucleotides which encode a gram positive microorganism MP, or fragments thereof, or fusion proteins or polynucleotide homologue sequences that encode amino acid variants of *B. subtilis* MP, may be used to generate recombinant DNA molecules that direct their expression in host cells. In a preferred embodiment, the gram positive host cell belongs to the genus *Bacillus*. In a further preferred embodiment, the gram positive host cell is *B. subtilis*.

As will be understood by those of skill in the art, it may be advantageous to produce polynucleotide sequences possessing non-naturally occurring codons. Codons preferred by a particular gram positive host cell (Murray, E. et al., (1989), *Nuc. Acids Res.,* 17:477–508) can be selected, for example, to increase the rate of expression or to produce recombinant RNA transcripts having desirable properties, such as a longer half-life, than transcripts produced from a naturally occurring sequence.

Altered MP polynucleotide sequences which may be used in accordance with the invention include deletions, insertions or substitutions of different nucleotide residues resulting in a polynucleotide that encodes the same or a functionally equivalent MP homologue, respectively. As used herein a "deletion" is defined as a change in the nucleotide sequence of the MP resulting in the absence of one or more amino acid residues.

As used herein, an "insertion" or "addition" is that change in the nucleotide sequence which results in the addition of one or more amino acid residues as compared to the naturally occurring MP.

As used herein, "substitution" results from the replacement of one or more nucleotides or amino acids by different nucleotides or amino acids, respectively. The change(s) in the nucleotides(s) can either result in a change in the amino acid sequence or not.

The encoded protein may also show deletions, insertions or substitutions of amino acid residues which produce a silent change and result in a functionally equivalent MP variant. Deliberate amino acid substitutions may be made on the basis of similarity in polarity, charge, solubility, hydrophobicity, hydrophilicity, and/or the amphipathic nature of the residues as long as the variant retains its proteolytic ability. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The MP polynucleotides of the present invention may be engineered in order to modify the cloning, processing and/or expression of the gene product. For example, mutations may be introduced using techniques which are well known in the art, i.e., site-directed mutagenesis to insert new restriction sites, to alter glycosylation patterns or to change codon preference, for example.

In one embodiment of the present invention, a gram positive microorganism MP polynucleotide may be ligated to a heterologous sequence to encode a fusion protein. A fusion protein may also be engineered to contain a cleavage site located between the metalloprotease nucleotide sequence and the heterologous protein sequence, so that the metalloprotease may be cleaved and purified away from the heterologous moiety.

IV. Vector Sequences

Expression vectors used in expressing the metalloproteases of the present invention in gram positive microorganisms comprise at least one promoter associated with MP, which promoter is functional in the host cell. In one embodiment of the present invention, the promoter is the wild-type promoter for the selected metalloprotease and in another embodiment of the present invention, the promoter is heterologous to the metalloprotease, but still functional in the host cell. In one preferred embodiment of the present invention, nucleic acid encoding the metalloprotease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term "selectable marker" refers to a gene capable of expression in the gram positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production Bacillus subtilis MP or MP homologues including bacterial, fungal, mammalian and insects cells. General transformation procedures are taught in *Current Protocols In Molecular Biology*, (Vol. 1, edited by Ausubel et al., John Wiley & Sons, Inc., 1987, Chapter 9) and include calcium phosphate methods, transformation using DEAE-Dextran and electroporation. Plant transformation methods are taught in Rodriquez (WO 95/14099, published 26 May 1995).

In a preferred embodiment, the host cell is a gram positive microorganism and in another preferred embodiment, the host cell is *Bacillus*. In one embodiment of the present invention, nucleic acid encoding one or more metalloprotease(s) of the present invention is introduced into a host cell via an expression vector capable of replicating within the *Bacillus* host cell. Suitable replicating plasmids for *Bacillus* are described in *Molecular Biological Methods for Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a metalloprotease(s) of the present invention is stably integrated into the microorganism genome. Preferred host cells are gram positive host cells. Another preferred host is *Bacillus*. Another preferred host is *Bacillus subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., *Plasmid*, 2:555–571 (1979); Haima et al., *Mol. Gen. Genet.*, 223:185–191 (1990); Weinrauch et al., *J. Bacteriol.*, 154(3):1077–1087 (1983); and Weinrauch et al., *J. Bacteriol.*, 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979), *Mol. Gen. Genet.*, 168:111–115; for *B. megaterium* in Vorobjeva et al., (1980), *FEMS Microbiol. Letters*, 7:261–263; for *B. amyloliquefaciens* in Smith et al., (1986), *Appl. and Env. Microbiol.*, 51:634; for *B. thuringiensis* in Fisher et al., (1981), *Arch. Microbiol.*, 139:213–217; for *B. sphaericus* in McDonald, (1984), *J. Gen. Microbiol.*, 130:203; and *B. larvae* in Bakhiet et al., (1985, Appl. Environ. Microbiol. 49:577). Mann et al., (1986, *Current Microbiol.*, 13:131–135) report on transformation of *Bacillus* protoplasts and Holubova, (1985), *Folia Microbiol.*, 30:97) disclose methods for introducing DNA into protoplasts using DNA containing liposomes.

VI. Identification of Transformants

Whether a host cell has been transformed with a mutated or a naturally occurring gene encoding a gram positive MP, detection of the presence/absence of marker gene expression can suggest whether the gene of interest is present. However, its expression should be confirmed. For example, if the nucleic acid encoding a metalloprotease is inserted within a marker gene sequence, recombinant cells containing the insert can be identified by the absence of marker gene function. Alternatively, a marker gene can be placed in tandem with nucleic acid encoding the metalloprotease under the control of a single promoter. Expression of the marker gene in response to induction or selection usually indicates expression of the metalloprotease as well.

Alternatively, host cells which contain the coding sequence for a metalloprotease and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the metalloprotease polynucleotide sequence can be detected by DNA-DNA or DNA-RNA hybridization or amplification using probes, portions or fragments of *B. subtilis* MP.

VII. Assay of Protease Activity

There are various assays known to those of skill in the art for detecting and measuring protease activity. There are assays based upon the release of acid-soluble peptides from casein or hemoglobin measured as absorbance at 280 nm or calorimetrically using the Folin method (Berg meyer, et al., 1984, *Methods of Enzymatic Analysis*, Vol. 5, Peptidases, Proteinases and their Inhibitors, Verlag Chemie, Weinheim). Other assays involve the solubilization of chromogenic substrates (Ward, 1983, Proteinases, in *Microbial Enzymes and Biotechnology*, (W. M. Fogarty, ed.), Applied Science, London, pp. 251–317).

VII. Secretion of Recombinant Proteins

Means for determining the levels of secretion of a heterologous or homologous protein in a gram positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton, R. et al., (1990, *Serological Methods, a Laboratory Manual*, APS Press, St. Paul Minn.) and Maddox, Del. et al., (1983, *J. Exp. Med.*, 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp. (Cleveland Ohio.) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram positive host cell comprising a mutation or deletion of the metalloprotease activity will be secreted into the culture media. Other recombinant constructions may join the heterologous or homologous polynucleotide sequences to a nucleotide sequence encoding a polypeptide domain which will facilitate purification of soluble proteins (Kroll, DJ. et al., (1993), *DNA Cell Biol.*, 12:441–53).

Such purification facilitating domains include, but are not limited to, metal chelating peptides such as histidine-tryptophan modules that allow purification on immobilized metals (Porath, J., (1992), *Protein Ex pr. Purif.* 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention

MP and Genetically Engineered Host Cells

The present invention provides genetically engineered host cells comprising mutations, preferably non-revertable mutations, or deletions in the naturally occurring gene encoding MP such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is further genetically engineered to produce a desired protein or polypeptide. In a preferred embodiment, the host cell is a *Bacillus*. In a further preferred embodiment, the host cell is a *Bacillus subtilis*.

In an alternative embodiment, a host cell is genetically engineered to produce a gram positive MP. In a preferred embodiment, the host cell is grown under large scale fermentation conditions. In another preferred embodiment, the MP is isolated and/or purified and used in the textile industry, the feed industry and in cleaning compositions such as detergents.

As noted, MP can be useful in formulating various cleaning compositions. A number of known compounds are suitable surfactants useful in compositions comprising the MP of the invention. These include nonionic, anionic, cationic, anionic or zwitterionic detergents, as disclosed in U.S. Pat. Nos. 4,404,128 and 4,261,868. A suitable detergent formulation is that described in Example 7 of U.S. Pat. No. 5,204,015. The art is familiar with the different formulations which can be used as cleaning compositions. In addition, MP can be used, for example, in bar or liquid soap applications, dishcare formulations, contact lens cleaning solutions or products, peptide hydrolysis, waste treatment, textile applications, as fusion-cleavage enzymes in protein production, etc. MP may comprise enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

MP can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of MP to conventional cleaning compositions does not create any special use limitation. In other words, any temperature and pH suitable for the detergent is also suitable for the present compositions as long as the pH is within the above range, and the temperature is below the described MP's denaturing temperature. In addition, MP can be used in a cleaning composition without detergents, again either alone or in combination with builders and stabilizers.

Proteases can be included in animal feed such as part of animal feed additives as described in, for example, U.S. Pat. Nos. 5,612,055; 5,314,692; and 5,147,642.

One aspect of the invention is a composition for the treatment of a textile that includes MP. The composition can be used to treat for example silk or wool as described in publications such as RD 216,034; EP 134,267; U.S. Pat. No. 4,533,359; and EP 344,259.

MP Polynucleotides

A *B. subtlis* MP polynucleotide, or any part thereof, provides the basis for detecting the presence of gram positive microorganism MP polynucleotide homologues through hybridization techniques and PCR technology.

Accordingly, one aspect of the present invention is to provide for nucleic acid hybridization and PCR probes which can be used to detect polynucleotide sequences, including genomic and cDNA sequences, encoding gram positive MP or portions thereof.

The manner and method of carrying out the present invention may be more fully understood by those of skill in the art by reference to the following examples, which examples are not intended in any manner to limit the scope of the present invention or of the claims directed thereto

EXAMPLE I

Preparation of a Genomic Library

The following example illustrates the preparation of a *Bacillus* genomic library.

Genomic DNA from *Bacillus* cells is prepared as taught in *Current Protocols In Molecular Biology*, Vol. 1, edited by Ausubel et al., John Wiley & Sons, Inc., 1987, Chapter 2. 4.1. Generally, *Bacillus* cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the *Bacillus* genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested *Bacillus* genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram Positive Microorganisms

The following example describes the detection of gram positive microorganism MP.

DNA derived from a gram positive microorganism is prepared according to the methods disclosed in *Current Protocols in Molecular Biology,* Chap. 2 or 3. The nucleic acid is subjected to hybridization and/or PCR amplification with a probe or primer derived from MP.

The nucleic acid probe is labeled by combining 50 pmol of the nucleic acid and 250 mCi of [gamma$^{32}$P] adenosine triphosphate (Amersham, Chicago Ill.) and T4 polynucleotide kinase (DuPont NEN®, Boston Mass.). The labeled probe is purified with Sephadex G-25 superfine resin column (Pharmacia). A portion containing 10$^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologues of *B. subtilis* MP. The homologues are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

---

We claim:

1. A cleaning composition comprising a metalloprotease comprising the amino acid shown in SEQ ID NO: 2.

2. The cleaning composition of claim 1, wherein said metalloprotease is encoded by a gene that hybridizes with the nucleic acid shown in SEQ ID NO:1, under low stringency conditions.

3. The cleaning composition of claim 2, wherein the hybridization takes places under high stringency conditions.

4. An animal feed comprising a metalloprotease comprising the amino acid shown in SEQ ID NO: 2.

5. The animal feed of claim 4, wherein said metalloprotease is encoded by a gene that hybridizes with the nucleic acid shown in SEQ ID NO:1, under low stringency conditions.

6. The animal feed of claim 5, wherein said hybridization takes places under high stringency conditions.

7. A textile treatment composition comprising a metalloprotease comprising the amino acid shown In SEQ ID NO: 2.

8. The textile treatment composition of claim 7, wherein the hybridization takes places under high stringency conditions.

* * * * *

SEQUENCE LISTING

<160> NUMBER OF SEQ ID NOS: 4

<210> SEQ ID NO 1
<211> LENGTH: 1450
<212> TYPE: DNA
<213> ORGANISM: Bacillus subtilis
<220> FEATURE:
<221> NAME/KEY: CDS
<222> LOCATION: (128)...(1315)

<400> SEQUENCE: 1

```
tcccgtcgcg attggccttt tggtgacaac cctcgcagct gtgatgatgc tttaaaacag        60
catgagttga aatattcaga cttttctat acaatcatgg aaaagcatag aaaggggga        120 agcggct ttg tcc ata tcc aca ctg cag aaa gag ata aac aaa cag ctc         169
        Leu Ser Ile Ser Thr Leu Gln Lys Glu Ile Asn Lys Gln Leu
        1               5                   10 gac ggc tgt ttt gaa gaa atg gtt gag atc agg cgc cat ttt cat atg         217
Asp Gly Cys Phe Glu Glu Met Val Glu Ile Arg Arg His Phe His Met
15                  20                  25                  30 tat cct gag ctc tca ttt caa gaa gaa aaa acc gcc gca ttt att gct         265
Tyr Pro Glu Leu Ser Phe Gln Glu Glu Lys Thr Ala Ala Phe Ile Ala
                35                  40                  45 tcc tat tat gaa tcg tta gga gtc cca atc cgc aca aac gtt ggc ggt         313
Ser Tyr Tyr Glu Ser Leu Gly Val Pro Ile Arg Thr Asn Val Gly Gly
            50                  55                  60 aga ggg gtt tta gca aat ata gaa gga agc gaa ccc ggc cct aca gtc         361
Arg Gly Val Leu Ala Asn Ile Glu Gly Ser Glu Pro Gly Pro Thr Val
        65                  70                  75 gct ttg agg gcc gac ttt gac gct ctc cca ttc aag atg aaa aaa gat         409
Ala Leu Arg Ala Asp Phe Asp Ala Leu Pro Phe Lys Met Lys Lys Asp
    80                  85                  90 gtc cct tac gcc tcc aaa gtg cct ggt gtc atg cat gca tgc ggc cac         457
```

```
                Val Pro Tyr Ala Ser Lys Val Pro Gly Val Met His Ala Cys Gly His
                 95                 100                 105                 110 gac ggc cac acc gca gct ctt ctc gca gtg gcc aag gtc ctt cac caa              505
Asp Gly His Thr Ala Ala Leu Leu Ala Val Ala Lys Val Leu His Gln
            115                 120                 125 aac aga cat gaa ctg aag gga aca ttt gtg atg atc cac cag cat gca              553
Asn Arg His Glu Leu Lys Gly Thr Phe Val Met Ile His Gln His Ala
        130                 135                 140 gaa gaa tat tat cct gga ggc gca aag cca atg att gat gac gga tgt              601
Glu Glu Tyr Tyr Pro Gly Gly Ala Lys Pro Met Ile Asp Asp Gly Cys
            145                 150                 155 ctc gaa aac acg gat gtg ata ttc ggc act cat ctt tgg gca act gag              649
Leu Glu Asn Thr Asp Val Ile Phe Gly Thr His Leu Trp Ala Thr Glu
160                 165                 170 ccg ctc gga act att ctc tgc cgc ccc ggc gcc gta atg gcg gcg gca              697
Pro Leu Gly Thr Ile Leu Cys Arg Pro Gly Ala Val Met Ala Ala Ala
175                 180                 185                 190 gac cga ttt acg att aaa gtc ttc gga aag ggc ggc cac ggc gct cat              745
Asp Arg Phe Thr Ile Lys Val Phe Gly Lys Gly Gly His Gly Ala His
                195                 200                 205 ccg cat gat act aaa gac gcc gtc cta atc ggt tcg caa atc gtt tcc              793
Pro His Asp Thr Lys Asp Ala Val Leu Ile Gly Ser Gln Ile Val Ser
        210                 215                 220 tct ttg cag cac att gtc agc cgc aaa gtc aat ccg att caa tcc gcc              841
Ser Leu Gln His Ile Val Ser Arg Lys Val Asn Pro Ile Gln Ser Ala
            225                 230                 235 gtc att tcg aca ggc tcc ttc atc gcc gac aat ccg ttt aat gtc atc              889
Val Ile Ser Thr Gly Ser Phe Ile Ala Asp Asn Pro Phe Asn Val Ile
240                 245                 250 gca gac caa gca gta ctc atc ggc aca gcg cgt tct ttt gat gaa aat              937
Ala Asp Gln Ala Val Leu Ile Gly Thr Ala Arg Ser Phe Asp Glu Asn
255                 260                 265                 270 gtc cgg gac att ctg gag aaa gaa att gaa gcg gtt gta aaa gga ata              985
Val Arg Asp Ile Leu Glu Lys Glu Ile Glu Ala Val Val Lys Gly Ile
                275                 280                 285 tgc agc atg cac ggc gcg tcc tat gag tac acc tat gaa cag ggt tat             1033
Cys Ser Met His Gly Ala Ser Tyr Glu Tyr Thr Tyr Glu Gln Gly Tyr
        290                 295                 300 cca gcg gtt gtg aac cat cct gca gaa acg aac cac ttg gtg agc acc             1081
Pro Ala Val Val Asn His Pro Ala Glu Thr Asn His Leu Val Ser Thr
            305                 310                 315 gca aag aat acc gag ggc gtt cag cag gtc att gac ggt gaa cca caa             1129
Ala Lys Asn Thr Glu Gly Val Gln Gln Val Ile Asp Gly Glu Pro Gln
320                 325                 330 atg ggc ggc gag gat ttt gct tat tac tta caa aac gtg aag ggc act             1177
Met Gly Gly Glu Asp Phe Ala Tyr Tyr Leu Gln Asn Val Lys Gly Thr
335                 340                 345                 350 ttt ttc ttt aca ggc gcc gct ccc gaa cag cca gag cga gtc tat tcc             1225
Phe Phe Phe Thr Gly Ala Ala Pro Glu Gln Pro Glu Arg Val Tyr Ser
                355                 360                 365 cac cac cat ccg aaa ttt gat atc aac gaa aaa gcc atg ctg aca gcg             1273
His His His Pro Lys Phe Asp Ile Asn Glu Lys Ala Met Leu Thr Ala
        370                 375                 380 gcc aag gtc ctt gcc ggc gct gcg atc acc tat cat cag cta                     1315
Ala Lys Val Leu Ala Gly Ala Ala Ile Thr Tyr His Gln Leu
            385                 390                 395 taaaaaaaca gccggagtgt ttattctccg gctgtttcct ttaatatcct cagatgaaaa           1375
acatgtcttg ccgtttctcc aagctgagca agcagcttat aattggcaat tccgccgact           1435
```

```
gccgctccta cgccc                                               1450
```

<210> SEQ ID NO 2
<211> LENGTH: 396
<212> TYPE: PRT
<213> ORGANISM: Bacillus subtilis

<400> SEQUENCE: 2

| Leu | Ser | Ile | Ser | Thr | Leu | Gln | Lys | Glu | Ile | Asn | Lys | Gln | Leu | Asp | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Phe | Glu | Glu | Met | Val | Glu | Ile | Arg | Arg | His | Phe | His | Met | Tyr | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Leu | Ser | Phe | Gln | Glu | Lys | Thr | Ala | Ala | Phe | Ile | Ala | Ser | Tyr |
|-----|-----|-----|-----|-----|-----|-----|-----|-----|-----|-----|-----|-----|-----|-----|
|     |     | 35  |     |     |     | 40  |     |     |     | 45  |     |     |     |     |

| Tyr | Glu | Ser | Leu | Gly | Val | Pro | Ile | Arg | Thr | Asn | Val | Gly | Gly | Arg | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Val | Leu | Ala | Asn | Ile | Glu | Gly | Ser | Glu | Pro | Gly | Pro | Thr | Val | Ala | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Ala | Asp | Phe | Asp | Ala | Leu | Pro | Phe | Lys | Met | Lys | Lys | Asp | Val | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Ala | Ser | Lys | Val | Pro | Gly | Val | Met | His | Ala | Cys | Gly | His | Asp | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| His | Thr | Ala | Ala | Leu | Leu | Ala | Val | Ala | Lys | Val | Leu | His | Gln | Asn | Arg |
|-----|-----|-----|-----|-----|-----|-----|-----|-----|-----|-----|-----|-----|-----|-----|-----|
|     |     | 115 |     |     |     | 120 |     |     |     |     | 125 |     |     |     |     |

| His | Glu | Leu | Lys | Gly | Thr | Phe | Val | Met | Ile | His | Gln | His | Ala | Glu | Glu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Tyr | Tyr | Pro | Gly | Gly | Ala | Lys | Pro | Met | Ile | Asp | Asp | Gly | Cys | Leu | Glu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asn | Thr | Asp | Val | Ile | Phe | Gly | Thr | His | Leu | Trp | Ala | Thr | Glu | Pro | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | Thr | Ile | Leu | Cys | Arg | Pro | Gly | Ala | Val | Met | Ala | Ala | Ala | Asp | Arg |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Phe | Thr | Ile | Lys | Val | Phe | Gly | Lys | Gly | Gly | His | Gly | Ala | His | Pro | His |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asp | Thr | Lys | Asp | Ala | Val | Leu | Ile | Gly | Ser | Gln | Ile | Val | Ser | Ser | Leu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | His | Ile | Val | Ser | Arg | Lys | Val | Asn | Pro | Ile | Gln | Ser | Ala | Val | Ile |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ser | Thr | Gly | Ser | Phe | Ile | Ala | Asp | Asn | Pro | Phe | Asn | Val | Ile | Ala | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gln | Ala | Val | Leu | Ile | Gly | Thr | Ala | Arg | Ser | Phe | Asp | Glu | Asn | Val | Arg |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Asp | Ile | Leu | Glu | Lys | Glu | Ile | Glu | Ala | Val | Val | Lys | Gly | Ile | Cys | Ser |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Met | His | Gly | Ala | Ser | Tyr | Glu | Tyr | Thr | Tyr | Glu | Gln | Gly | Tyr | Pro | Ala |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Val | Val | Asn | His | Pro | Ala | Glu | Thr | Asn | His | Leu | Val | Ser | Thr | Ala | Lys |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Asn | Thr | Glu | Gly | Val | Gln | Gln | Val | Ile | Asp | Gly | Glu | Pro | Gln | Met | Gly |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Gly | Glu | Asp | Phe | Ala | Tyr | Tyr | Leu | Gln | Asn | Val | Lys | Gly | Thr | Phe | Phe |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Phe | Thr | Gly | Ala | Ala | Pro | Glu | Gln | Pro | Glu | Arg | Val | Tyr | Ser | His | His |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

His Pro Lys Phe Asp Ile Asn Glu Lys Ala Met Leu Thr Ala Ala Lys
    370                 375                 380

Val Leu Ala Gly Ala Ala Ile Thr Tyr His Gln Leu
385                 390                 395

<210> SEQ ID NO 3
<211> LENGTH: 383
<212> TYPE: PRT
<213> ORGANISM: Campylobacter jejuni

<400> SEQUENCE: 3

Met Asn Leu Ile Pro Glu Ile Leu Asp Leu Gln Gly Glu Phe Glu Lys
  1               5                  10                  15

Ile Arg His Gln Ile His Glu Asn Pro Glu Leu Gly Phe Asp Glu Leu
                 20                  25                  30

Cys Thr Ala Lys Leu Val Ala Gln Lys Leu Lys Glu Phe Gly Tyr Glu
             35                  40                  45

Val Tyr Glu Glu Ile Gly Lys Thr Gly Val Val Gly Val Leu Lys Lys
 50                  55                  60

Gly Asn Ser Asp Lys Lys Ile Gly Leu Arg Ala Asp Met Asp Ala Leu
 65                  70                  75                  80

Pro Leu Gln Glu Cys Thr Asn Leu Pro Tyr Lys Ser Lys Lys Glu Asn
                 85                  90                  95

Val Met His Ala Cys Gly His Asp Gly His Thr Thr Ser Leu Leu Leu
                100                 105                 110

Ala Ala Lys Tyr Leu Ala Ser Gln Asn Phe Asn Gly Thr Leu Asn Leu
            115                 120                 125

Tyr Phe Gln Pro Ala Glu Glu Gly Leu Gly Gly Ala Lys Ala Met Ile
130                 135                 140

Glu Asp Gly Leu Phe Glu Lys Phe Asp Ser Asp Tyr Val Phe Gly Trp
145                 150                 155                 160

His Asn Met Pro Phe Gly Ser Asp Lys Lys Phe Tyr Leu Lys Lys Gly
                165                 170                 175

Ala Met Met Ala Ser Ser Asp Ser Tyr Ser Ile Glu Val Ile Gly Arg
            180                 185                 190

Gly Gly His Gly Ser Ala Pro Glu Lys Ala Lys Asp Pro Ile Tyr Ala
        195                 200                 205

Ala Ser Leu Leu Val Val Ala Leu Gln Ser Ile Val Ser Arg Asn Val
210                 215                 220

Asp Pro Gln Asn Ser Ala Val Val Ser Ile Gly Ala Phe Asn Ala Gly
225                 230                 235                 240

His Ala Phe Asn Ile Ile Pro Asp Ile Val Thr Ile Lys Met Ser Val
                245                 250                 255

Arg Ala Leu Asp Asn Glu Thr Arg Lys Leu Thr Glu Glu Lys Ile Tyr
            260                 265                 270

Lys Ile Cys Lys Gly Leu Ala Gln Ala Asn Asp Ile Glu Ile Lys Ile
        275                 280                 285

Asn Lys Asn Val Val Ala Pro Val Thr Met Asn Asn Asp Glu Ala Val
290                 295                 300

Asp Phe Ala Ser Glu Val Ala Lys Glu Leu Phe Gly Glu Lys Asn Cys
305                 310                 315                 320

Glu Phe Asn His Arg Pro Leu Met Ala Ser Glu Asp Phe Gly Phe Phe
                325                 330                 335

Cys Glu Met Lys Lys Cys Ala Tyr Ala Phe Leu Glu Asn Glu Asn Asp
            340                 345                 350

```
Ile Tyr Leu His Asn Ser Ser Tyr Val Phe Asn Asp Lys Leu Leu Ala
        355                 360                 365

Arg Ala Ala Ser Tyr Tyr Ala Lys Leu Ala Leu Lys Tyr Leu Lys
370                 375                 380

<210> SEQ ID NO 4
<211> LENGTH: 396
<212> TYPE: PRT
<213> ORGANISM: Bacillus subtilis

<400> SEQUENCE: 4

Met Ser Ile Ser Thr Leu Gln Lys Glu Ile Asn Lys Gln Leu Asp Gly
1               5                   10                  15

Cys Phe Glu Glu Met Val Glu Ile Arg Arg His Phe His Met Tyr Pro
            20                  25                  30

Glu Leu Ser Phe Gln Glu Glu Lys Thr Ala Ala Phe Ile Ala Ser Tyr
        35                  40                  45

Tyr Glu Ser Leu Gly Val Pro Ile Arg Thr Asn Val Gly Gly Arg Gly
    50                  55                  60

Val Leu Ala Asn Ile Glu Gly Ser Glu Pro Gly Pro Thr Val Ala Leu
65                  70                  75                  80

Arg Ala Asp Phe Asp Ala Leu Pro Phe Lys Met Lys Lys Asp Val Pro
                85                  90                  95

Tyr Ala Ser Lys Val Pro Gly Val Met His Ala Cys Gly His Asp Gly
            100                 105                 110

His Thr Ala Ala Leu Leu Ala Val Ala Lys Val Leu His Gln Asn Arg
        115                 120                 125

His Glu Leu Lys Gly Thr Phe Val Met Ile His Gln His Ala Glu Glu
    130                 135                 140

Tyr Tyr Pro Gly Gly Ala Lys Pro Met Ile Asp Asp Gly Cys Leu Glu
145                 150                 155                 160

Asn Thr Asp Val Ile Phe Gly Thr His Leu Trp Ala Thr Glu Pro Leu
                165                 170                 175

Gly Thr Ile Leu Cys Arg Pro Gly Ala Val Met Ala Ala Ala Asp Arg
            180                 185                 190

Phe Thr Ile Lys Val Phe Gly Lys Gly Gly His Gly Ala His Pro His
        195                 200                 205

Asp Thr Lys Asp Ala Val Leu Ile Gly Ser Gln Ile Val Ser Ser Leu
    210                 215                 220

Gln His Ile Val Ser Arg Lys Val Asn Pro Ile Gln Ser Ala Val Ile
225                 230                 235                 240

Ser Thr Gly Ser Phe Ile Ala Asp Asn Pro Phe Asn Val Ile Ala Asp
                245                 250                 255

Gln Ala Val Leu Ile Gly Thr Ala Arg Ser Phe Asp Glu Asn Val Arg
            260                 265                 270

Asp Ile Leu Glu Lys Glu Ile Glu Ala Val Val Lys Gly Ile Cys Ser
        275                 280                 285

Met His Gly Ala Ser Tyr Glu Tyr Thr Tyr Glu Gln Gly Tyr Pro Ala
    290                 295                 300

Val Val Asn His Pro Ala Glu Thr Asn His Leu Val Ser Thr Ala Lys
305                 310                 315                 320

Asn Thr Glu Gly Val Gln Gln Val Ile Asp Gly Glu Pro Gln Met Gly
                325                 330                 335

Gly Glu Asp Phe Ala Tyr Tyr Leu Gln Asn Val Lys Gly Thr Phe Phe
```

```
                   340                 345                 350
    Phe Thr Gly Ala Ala Pro Glu Gln Pro Glu Arg Val Tyr Ser His His
            355                 360                 365

His Pro Lys Phe Asp Ile Asn Glu Lys Ala Met Leu Thr Ala Ala Lys
        370                 375                 380

Val Leu Ala Gly Ala Ala Ile Thr Tyr His Gln Leu
    385             390             395
```